US008884028B2

(12) United States Patent  
Zumpe et al.

(10) Patent No.: US 8,884,028 B2
(45) Date of Patent: Nov. 11, 2014

(54) PROCESS FOR PREPARING ALKYL 2-ALKOXYMETHYLENE-4,4-DIFLUORO-3-OXOBUTYRATES

(75) Inventors: Franz Linus Zumpe, Munchwilen (CH); Ralf Kohlbrenner, Munchwilen (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 13/635,346

(22) PCT Filed: Mar. 14, 2011

(86) PCT No.: PCT/EP2011/053786
§ 371 (c)(1), (2), (4) Date: Sep. 14, 2012

(87) PCT Pub. No.: WO2011/113789
PCT Pub. Date: Sep. 22, 2011

(65) Prior Publication Data
US 2013/0012722 A1    Jan. 10, 2013

(30) Foreign Application Priority Data
Mar. 15, 2010    (GB) .................................. 1004301.6

(51) Int. Cl.
C07C 67/343 (2006.01)
C07C 69/738 (2006.01)
C07D 231/14 (2006.01)
C07D 409/12 (2006.01)

(52) U.S. Cl.
CPC ............ C07D 231/14 (2013.01); C07C 67/343 (2013.01); C07C 69/738 (2013.01); C07D 409/12 (2013.01)
USPC ...................... 548/365.7; 548/374.1; 560/174

(58) Field of Classification Search
None
See application file for complete search history.

(56) References Cited
U.S. PATENT DOCUMENTS
8,207,354 B2 *    6/2012    Maywald et al. .......... 548/374.1
* cited by examiner Primary Examiner — Kamal Saeed
(74) Attorney, Agent, or Firm — Brian D. McAlhaney

(57) ABSTRACT

The present invention relates to a process for preparing a compound of formula (II) wherein $R^1$ is $CF_3$, $CF_2H$ or $CFH_2$, and $R^2$ and $R^3$ are both independently $C_1$-$C_6$ alkyl, comprising a) reacting compounds of formula (IV), (V) and (VI) wherein R3 is as defined for the compound of formula (II), $R^4OM$ (V) wherein M is a lithium, sodium or potassium ion and R4 is $C_1$-$C_6$ alkyl, and (VI) wherein R1 is as defined for the compound of formula (II) and R5 is CrC6 alkyl, to form an enolate of formula (VII) wherein M is as defined for the compound of formula V and $R^1$ and $R^3$ are defined for the compound of formula (II), b) releasing the compound of formula (VIII) wherein $R^1$ and $R^3$ are as defined for the compound of formula (II), from the enolate of formula (VII) by means of an acid, and c) converting the compound of formula (VIII), in the presence of the salt formed from cation M and the anion of the acid in step b), to a compound of formula (II).

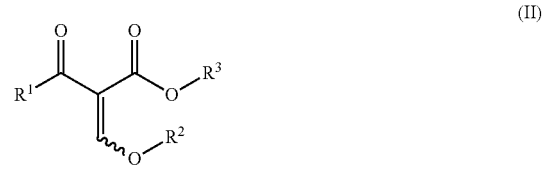

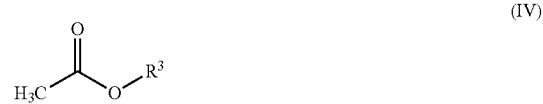

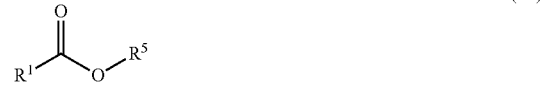

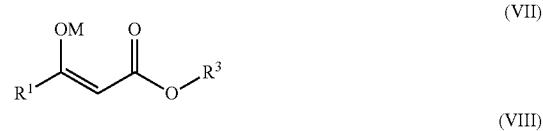

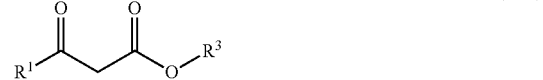

7 Claims, No Drawings

PROCESS FOR PREPARING ALKYL 2-ALKOXYMETHYLENE-4,4-DIFLUORO-3-OXOBUTYRATES

This application is a 371 of International Application No. PCT/EP2011/053786 filed Mar. 14, 2011, which claims priority to GB 1004301.6 filed Mar. 15, 2010, the contents of which are incorporated herein by reference.

The present invention relates to processes for the preparation of compounds of formula II

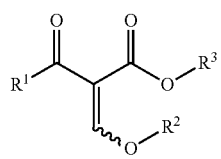
(II)

wherein $R^1$ is $CF_3$, $CF_2H$ or $CFH_2$, and $R^2$ and $R^3$ are both independently $C_1$-$C_6$ alkyl.

Certain compounds of formula II are useful intermediates in the synthesis of 3-difluoromethyl-1-methyl-1H-pyrazole-4-carboxylic acid, which is a key intermediate in the synthesis of fungicides such as Isopyrazam, Sedaxane, and others. Processes for the production of compounds of formula II are described, for example, in WO 2009/106619.

It has now surprisingly been found that the step of removing the salt following the protonation of the enolate in the process for producing compounds of formula II described in WO 2009/106619 is unnecessary. A reduction in the number of process steps potentially represents significant cost savings for commercial synthesis, e.g. by reducing cycle time and manufacturing costs.

In a first aspect the invention provides a process for preparing a compound of formula II

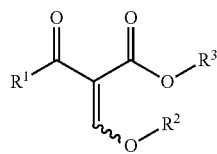
(II)

wherein $R^1$ is $CF_3$, $CF_2H$ or $CFH_2$, and $R^2$ and $R^3$ are both independently $C_1$-$C_6$ alkyl, comprising a) reacting compounds of formula (IV), (V) and (VI)

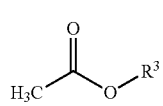
(IV)

wherein $R^3$ is as defined for the compound of formula II,

R$^4$OM (V)

wherein M is a lithium, sodium or potassium ion and $R^4$ is $C_1$-$C_6$ alkyl, and

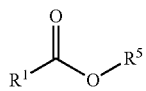
(VI)

wherein $R^1$ is as defined for the compound of formula II and $R^5$ is $C_1$-$C_6$ alkyl, to form an enolate of formula VII

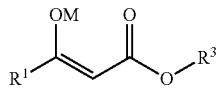
(VII)

wherein M is as defined for the compound of formula V and $R^1$ and $R^3$ are as defined for the compound of formula II, b) releasing the compound of formula VIII

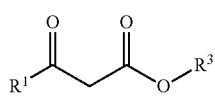
(VIII)

wherein $R^1$ and $R^3$ are as defined for the compound of formula II, from the enolate of formula VII by means of an acid, and c) converting the compound of formula VIII, in the presence of the salt formed from cation M and the anion of the acid in step b), to a compound of formula II.

In a further aspect, the invention provides a process for preparing a compound of formula III

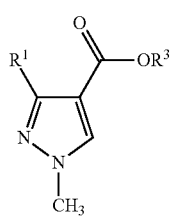
(III)

wherein $R^1$ is $CF_3$, $CF_2H$ or $CFH_2$, and $R^3$ is $C_1$-$C_6$ alkyl, comprising a) reacting compounds of formula (IV), (V) and (VI)

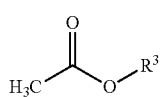
(IV)

wherein $R^3$ is as defined for the compound of formula III,

R$^4$OM (V)

wherein M is a lithium, sodium or potassium ion and $R^4$ is $C_1$-$C_6$ alkyl, and

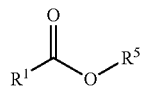

(VI)

wherein $R^1$ is as defined for the compound of formula III and $R^5$ is $C_1$-$C_6$ alkyl,
to form an enolate of formula VII

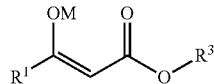

(VII)

wherein M is as defined for formula V and $R^1$ and $R^3$ are as defined for the compound of formula III, and
b) releasing the compound of formula VIII

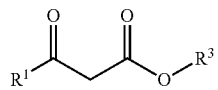

(VIII)

wherein $R^1$ and $R^3$ are as defined for the compound of formula III,
from the enolate of formula VII by means of an acid,
c) converting the compound of formula VIII, in the presence of the salt formed from cation M and the anion of the acid in step b), to a compound of formula II,

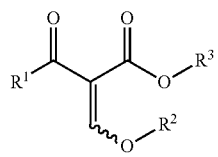

(II)

wherein $R^1$ and $R^3$ are as defined for the compound of formula III and $R^2$ is $C_1$-$C_6$ alkyl, and
d) reacting the compound of formula II with methylhydrazine in the presence of water to form a compound of formula III.

Preferably the process comprises the step
e) separating the compound of formula III from the salt formed from cation M and the anion of the acid in step b).

In a further aspect, the invention provides a process for preparing a compound of formula III

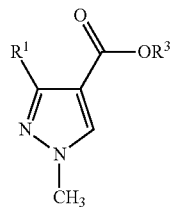

(III)

wherein $R^1$ is $CF_3$, $CF_2H$ or $CFH_2$, and $R^3$ is $C_1$-$C_6$ alkyl, comprising providing a mixture comprising a compound of formula II

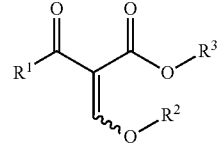

(II)

wherein $R^1$ and $R^3$ are as defined for the compound of formula III and $R^2$ is $C_1$-$C_6$ alkyl, and a salt and performing the steps
dd) reacting the mixture comprising the compound of formula II and the salt with methylhydrazine in the presence of water to form a compound of formula III; and
ee) separating the compound of formula III from the salt.
Preferably the salt is one as described below.
Steps dd) and ee) correspond to steps d) and e). Process conditions described for steps d) and e) also apply to steps dd) and ee).

Preferably step d) is carried out in the presence of a water-immiscible solvent and in step e) the compound of formula III is separated from the salt by separating the organic phase containing the compound of formula III from the aqueous phase containing the salt. This is particularly advantageous as it removes the requirement in the process for a salt filtration step, thereby significantly reducing investment costs.

The invention may include the step
f) converting the compound of formula III to a compound of formula I

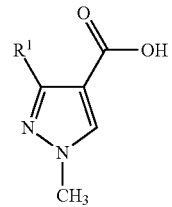

(I)

wherein $R^1$ is $CF_3$, $CF_2H$ or $CFH_2$.

Processes for the conversion of compounds of formula II to compounds of formula III and subsequently to compounds of formula I are described, for example, in WO 2008/145257 and EP 1854788. The starting compounds of formula IV, V and VI are commercially available or can be prepared according to known procedures.

In procedures in which the salt is removed prior to formation of compounds of formula II water is generally added to put the salt into a form which is more easily filtered. In the absence of water the salt may be present in a form which leads to long filtration times and which is not efficient for large scale production. However, the addition of water leads to disadvantages, for example increased consumption of feedstocks such as orthoester and acetic acid anhydride which increases costs. Because the methods of the invention do not require removal of salt prior to formation of compounds of formula II, it is not necessary to add water prior to step c) to aid filtration, thereby avoiding the disadvantages associated with addition of water.

Preferably, in step b) the release of the compound of formula VIII from the enolate of formula VII is carried out substantially in the absence of water, preferably in the absence of water.

Preferably, in step c) the compound of formula VIII is converted to a compound of formula II in the absence of an acid anhydride.

In a further aspect, the invention provides a process for preparing a compound of formula X

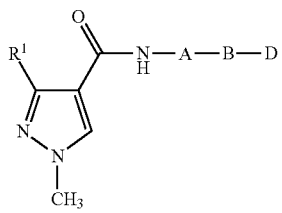
(X)

wherein $R^1$ is $CF_3$, $CF_2H$ or $CFH_2$,

A is thienyl, phenyl, or ethylene each optionally substituted by one to three groups independently selected from halogen, methyl and methoxy, B is a direct bond, cyclopropylene, an annelated bicyclo[2.2.1]heptane- or bicyclo[2.2.1]heptene ring, D is hydrogen, halogen, $C_1$-$C_6$ alkyl, $C_1$-$C_6$ haloalkyl, $C_1$-$C_6$ alkoxy, $C_1$-$C_6$ haloalkoxy, $C_3$-$C_6$ cycloalkyl, $C_1$-$C_6$ alkylidene, $C_1$-$C_6$ haloalkylidene, phenyl or phenyl optionally substituted by one to three substituents independently selected from halogen and trihalomethylthio, comprising preparing a compound of formula I

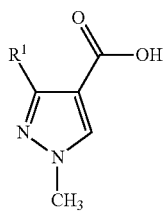
(I)

wherein $R^1$ is $CF_3$, $CF_2H$ or $CFH_2$, according to the invention, and g) reacting the compound of formula I with a compound of formula XI

H$_2$N-A-B-D    (XI)

wherein A, B and D are as defined for the compound of formula X.

The compound of formula X is preferably a compound of formula XII (Isopyrazam), a compound of formula XIII (Sedaxane), a compound of formula XIV, a compound of formula XV (Penthiopyrad), a compound of formula XVI (Bixafen), a compound of formula XVII (Fluxapyroxad), a compound of formula XVIII, or a compound of formula XIX.

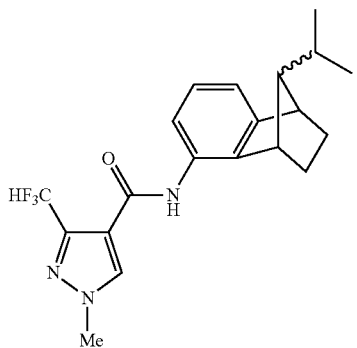
(XII)

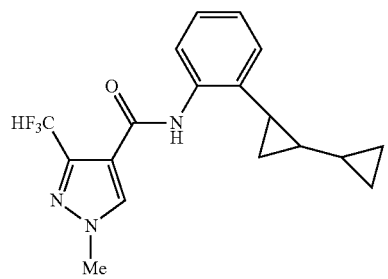
(XIII)

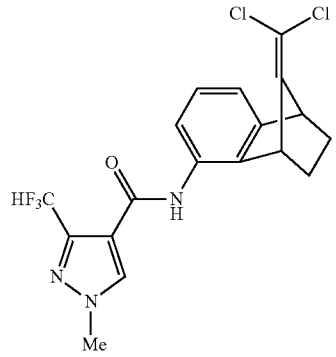
(XIV)

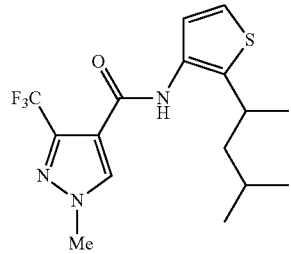
(XV)

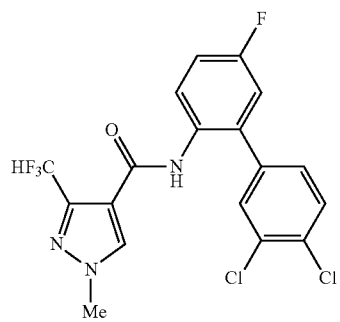
(XVI)

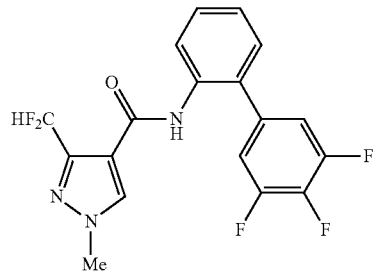
(XVII)

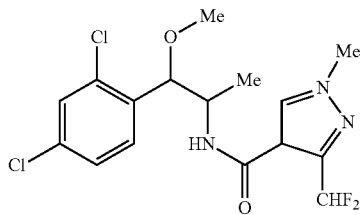

(XVIII)

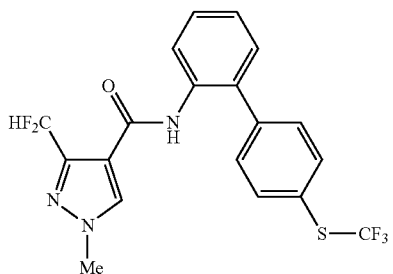

(XIX)

Isopyrazam, Sedaxane, Penthiopyrad, Fluxapyroxad and Bixafen are known fungicides. The compound of formula XIV is known, e.g. from WO 2007/048556, the compound of formula XVIII is known e.g. from WO 2010/000612, the compound of formula XIX is known e.g. from WO 2008/053044.

In a further aspect the invention provides a mixture comprising a compound of formula II

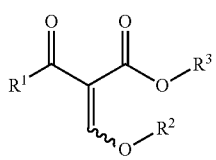

(II)

wherein $R^1$ is $CF_3$, $CF_2H$ or $CFH_2$, and $R^2$ and $R^3$ are both independently $C_1$-$C_6$ alkyl, and a salt. Preferably the mixture is a suspension in which the salt is a solid. Preferably the salt is one in which the cation is a lithium, sodium or potassium ion, e.g. the salt may be a lithium, sodium or potassium salt of chloride, bromide, iodide, sulphate, phosphate, nitrate, formate, acetate, propionate, citrate, oxalate, methanesulfonate or p-toluenesulfonate, preferably a lithium, sodium or potassium salt of chloride or sulphate.

The molar ratio of salt to compound of formula II is preferably in the range 0.8:1 to 1:0.5, usually about equimolar. Preferably the mixture is one obtainable according to the processes of the invention.

The alkyl groups may be straight-chain or branched and are, for example, methyl, ethyl, n-propyl, isopropyl, n-butyl, sec-butyl, isobutyl or tert-butyl, preferably methyl or ethyl.

Compounds of formula II occur in two isomers with regard to the double bond substituted by the alkoxy group —O—$R_2$: the E- and the Z-isomer. Both isomers or mixtures thereof can be used in the processes according to the invention.

Reference to compounds of formula VIII includes reference to the enol tautomer, any hydrated forms, and the hemiketals.

Preferably $R^1$ is $CF_2H$.

Preferably $R^2$, $R^3$, $R^4$, and $R^5$ are independently methyl or ethyl, more preferably ethyl.

Preferably M is sodium or potassium, more preferably sodium.

Process Step a):

In step a), preferably two of compounds IV, V and VI are initially charged and that mixture is reacted with the third component to form the enolate. Preferably, compounds of formula IV and formula VI are precharged and the compound of formula V is metered in. The reaction may be carried out in the presence of an additional organic solvent, but preferably the reaction is run without an additional solvent.

When present, the additional organic solvent is preferably inert in saponification reactions, thereby allowing said solvent to remain in the reaction mixture until step f). A solvent that is inert in saponification reactions means, for example, a solvent that is suitable for use in saponification reactions, e.g. it remains substantially unchanged during saponification reactions.

Examples of additional organic solvents which can be used in step a) are water-miscible solvents and water-immiscible solvents. Preferred additional solvents are water-immiscible. According to the invention "water-immiscible" means that when the organic solvent is mixed with water under the conditions of the process according to the invention two separate liquid phases are formed.

Preferred additional organic solvents are optionally halogenated aromatic hydrocarbon solvents, hydrocarbon solvents, alcohols or ether solvents. In said definitions, halogen is generally fluorine, chlorine, bromine and/or iodine, preferably fluorine, bromine and/or chlorine. Preferred "optionally halogenated aromatic hydrocarbon solvents" are benzene, toluene, ethylbenzene, xylenes, chlorobenzene, dichlorobenzene, mesitylene and mixtures thereof; more preferred are xylenes and mesitylene. Preferred hydrocarbon solvents are isoparaffinic fluids and mixtures of isoparaffinic fluids. Preferred alcohols are methanol, ethanol, 2-butoxyethanol, 2-ethoxyethanol, 2-methoxyethanol, propanol, isopropanol, 1-butanol, 2-butanol, isobutanol, tert-butanol, pentanols, hexanols, heptanols, octanols, isoamyl alcohol, benzyl alcohol, cyclohexanol, 1,3-butanediol, 1,4-butanediol, ethylene glycol, diethylene glycol, diethylene glycol ethyl ether, diethylene glycol methyl ether, more preferred are water-immiscible alcohols. Preferred "ether solvents" are diethoxymethane, dimethoxyethane, dioxane, ethylene glycol diethyl ether, diethylenediglycol dialkylethers such as 1-Methoxy-2-(2-methoxy-ethoxy)-ethane (diglyme), 1-Ethoxy-2-(2-ethoxy-ethoxy)-ethane, triglyme, anisole, diphenylether.

Preferably, the amount of the compound of formula IV is such that the reaction mixture with the compound of formula V and compound of formula VI, either in the presence of or without an additional solvent, gives rise to a readily stirrable suspension or to a homogeneous solution. Preferably, the molar ratio of compounds of formula IV to compounds of formula V is from 0.8:1 to 10:1, more preferably from 1:1 to 8:1, most preferably from 1:1 to 5:1. The molar ratio of the compound of the formula VI to the compound of formula IV is preferably from 1:0.7 to 1:15, more preferably from 1:1 to 1:10, even more preferably from 1:1 to 1:6. A person skilled in the art will be able to optimise the ratio of the compounds of formula IV, V and VI to increase reaction efficiency whilst minimising costs.

The compounds of formula V can be used in its solid state or as a solution in a suitable solvent, e.g. the corresponding alcohol.

The metered addition of compounds of formula IV, V and/or VI is typically performed within 0.1 to 20 hours, more preferably within 0.25 to 10 hours, even more preferably within 1 to 5 hours.

The reaction temperature for process step a) is generally from −25° C. up to the boiling point of the reaction mixture, more preferably from 0° C. to 80° C.

The reaction can be carried out under standard pressure or under slightly elevated or reduced pressure. Typically, the reaction is run under standard pressure.

Process Step b):

Process step b) may be carried out in the presence of an additional organic solvent as described for process step a), but preferably the reaction is run without an additional solvent.

In process step b) a compound of formula VIII is generally released from the enolate of formula VII by means of an inorganic acid such as hydrogen chloride, hydrogen bromide, hydrogen iodide, sulfuric acid, phosphoric acid, nitric acid or an organic acid such as formic acid, acetic acid, propionic acid, citric acid, oxalic acid, methanesulfonic acid or p-toluenesulfonic acid. Preferably the acid is hydrogen chloride.

In step b) 0.6 to 6 mol of acid per mol of compound of formula V may be used, preferably from 0.7 to 2.5 mol of acid per mol of (V), even more preferably 0.8 to 1.5 mol of acid per mol of (V).

Step b) may be performed at a temperature from −5° C. to the boiling point of the reaction mixture, preferably from 0° C. to 50° C.

Process step b) may be carried out at standard pressure or slightly elevated pressure up to about 3 bar.

Process Step c):

In process step c) the compound of formula VIII may be converted into the compound of formula II by reacting the compound of formula VIII with an orthoester, e.g. a compound of formula IX

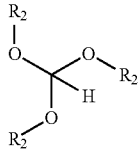

(IX)

wherein $R^2$ is as defined for the compound of formula II. An acid anhydride, e.g. acetic acid anhydride, may be used as a co-reagent, but preferably an acid anhydride is not used in the reaction.

Not using an acid anhydride simplifies the process and makes it safer. Using an acid anhydride leads to a distillate fraction which would contain the acid anhydride, the corresponding acid and the orthoester. These mixtures are known to be thermally instable, which raises safety issues. Furthermore, the possibility of recycling such a mixture is limited.

Preferably the compound of formula VIII is not isolated between steps b) and c), e.g. the crude mixture from step b) is carried through to step c).

Low boiling components within the crude mixture coming from steps a) and b) may be removed by distillation before running process step c). When the low boiling components are not distilled before carrying out process step c), they will usually be distilled under the reaction conditions of step c).

Preferably the molar ratio of orthoester, e.g. a compound of formula IX, to the compound of formula VIII may be from 1:1 to 30:1. Preferably there is an excess of orthoester compared to the compound of formula VIII as this can result in an improved yield. Preferably the molar ratio of the orthoester to the compound of formula VIII is at least 5:1, preferably at least 10:1. For example, the molar ratio of the orthoester to the compound of formula VIII is 5:1 to 30:1, preferably 10:1 to 20:1.

When used, the molar ratio of acid anhydride to compounds of formula VIII may be from 0:1 to 5:1, preferably from 0:1 to 2.5:1, more preferably from 0:1 to 1:1.

Step c) is normally carried out at temperatures from 20° C. to the boiling point of the reaction mixture, preferably from 50° C. to 150° C., even more preferably from 80° C. to 125° C.

Generally, step c) can be run at standard pressure, elevated pressure or reduced pressure. Preferably the reaction is run under reduced pressure, more preferably at from 0 mbar to 750 mbar. Running the reaction under reduced pressure also ensures that by-product, e.g. ethanol, being released during the reaction and coming from steps a) and b) is removed by distillation. This helps to reduce the amount of acetic acid anhydride needed, which not only captures any water present but also ethanol as well.

Before reacting the compound of formula II in process step d) the mixture comprising the compound of formula II may be concentrated, e.g. by distillation. Preferably said concentrating is performed in the presence of the salt formed from the cation M and the acid anion in step b). During concentrating excess reagents or solvents may be removed, e.g. excess orthoester. The distillation may be carried out under reduced pressure, preferably from 0 to 500 mbar, at a temperature that ensures constant boiling of the contents of the vessel.

The process may comprise performing step c) in the presence of a non-volatile acid, e.g. in order to maintain an acidic pH during the reaction. The non-volatile acid may be the same acid as the acid used in step b), or it may be a different acid. The non-volatile acid may be added after step b).

A non-volatile acid is for example any suitable acid that has a boiling point above 100° C. at 1 atm, more preferably above 110° C., more preferably above 120° C. Preferably the non-volatile acid is an organic acid, or a sulphur based acid or a phosphor based acid, e.g. acetic acid, propionic acid, sulphuric acid, phosphoric acid, or methanesulfonic acid.

Generally, at least 0.001 mol, preferably at least 0.01 mol of non-volatile acid per mol of compound V is used, e.g. up to the quantities used for process step b), e.g. when the acid used in step b) is a non-volatile acid.

The addition of the non-volatile acid is generally carried out at temperatures form −5° C. to the boiling point of the reaction mixture, preferably from 0° C. to 40° C. The addition time of the non-volatile acid is not particularly critical. The addition of the non-volatile acid can be carried out at standard pressure, slightly elevated or slightly reduced pressure. Preferably the addition is performed at standard pressure.

The process may also comprise concentrating a compound of formula VIII in a mixture comprising a compound of formula VIII by distillation in the presence of a non-volatile acid.

Process Step d):

In process step d), methylhydrazine can be used in equimolar amounts, in sub-equimolar amounts or in excess relative to compounds of formula II, preferably methylhydrazine is used in equimolar amounts. Thus the molar ratio of methyl hydrazine:compound of formula II is preferably from 1:0.8 to 1:1.2, preferably 1:1.

Methylhydrazine may be used in the form of an aqueous solution, such as a 35% (w/w) or 40% (w/w) aqueous solution. If 40% w/w methylhydrazine is used as a starting material it is preferred to add sufficient water to dilute the methylhydrazine to 35% w/w.

Preferably an organic solvent is used in step d), preferably one which is inert in saponification reactions so that said solvent may also be present in saponification step f).

Any organic solvent used in step d) is preferably water-immiscible. Preferred organic solvents are optionally halogenated aromatic hydrocarbon solvents, ketone solvents, optionally halogenated hydrocarbon solvents or ether solvents. In said definitions, halogen is generally fluorine, chlorine, bromine and/or iodine, preferably fluorine, bromine and/or chlorine. Preferred organic solvents are optionally halogenated aromatic hydrocarbon solvents, more preferred are aromatic hydrocarbon solvents, especially xylenes. Preferred "optionally halogenated aromatic hydrocarbon solvents" are benzene, toluene, xylenes, chlorobenzene, dichlorobenzene, mesitylene and mixtures thereof; more preferred are toluene and xylenes; most preferred are xylenes. Preferred "ketone solvent" is methylisobutylketone. Preferred "optionally halogenated hydrocarbon solvents" are pentane, hexane, octane, cyclohexane, methylcyclohexane, isoparaffinic fluids and mixtures of isoparaffinic fluids, chloroform and carbon tetrachloride; more preferred is cyclohexane. Preferred "ether solvent" is dioxane.

Process step d) is preferably carried out in a temperature range from −20° C. to 50° C., preferably from 0° C. to 50° C., especially from 10° C. to 25° C.

The reaction time for process step d) is generally from 15 minutes to 48 hours, preferably 15 minutes to 18 hours, more preferably 15 minutes to 5 hours or from 1 to 5 hours. Said step can be carried out at normal, elevated or reduced pressure. In one embodiment, said step is carried out at normal pressure.

The molar ratio of methylhydrazine to organic solvent is preferably from 1:1 to 1:20, more preferably 1:1 to 1:10, even more preferably from 1:1 to 1:6. The mass ratio of methylhydrazine 35% to organic solvent is preferably from 1:1 to 1:20, more preferably 1:1 to 1:5, even more preferably from 1:1 to 1.5. The molar ratio of compound of formula II to organic solvent is preferably from 1:1 to 1:20, more preferably 1:1 to 1:10, even more preferably from 1:2 to 1:6. The mass ratio of compound of formula II to organic solvent is preferably from 1:1 to 1:20, more preferably 1:1 to 1:5, even more preferably from 1:1 to 1:3.

An example of step d) is a process step comprising: preparing a solution comprising methyhydrazine in water and an organic solvent, preparing a suspension/solution of the compound of formula II in the organic solvent, and mixing the solution and the suspension or both solutions. The solution comprising methylhydrazine can be added to the suspension/solution of the compound of formula II in the organic solvent or vice versa. In one embodiment, the suspension/solution of the compound of formula II in the organic solvent is added to the solution comprising methylhydrazine.

Preferably step d) is performed in the presence of the salt formed from the cation M and the acid anion in step b).

Process Step f):

Process step f), saponification, may be carried out without isolation of compounds of formula III (e.g. the compounds of formula III are used in situ). Step f) can be carried out as described under step f1) and f2) (alkaline saponification) or under step f3) (acidic saponification).

Process Step f1):

Step f1) can be divided into two sub-steps: i) the formation of the anion of the compound for formula I ("the anion") by adding a base and ii) the formation of the compound of formula I ("the free acid") by later adding an acid.

The base is preferably selected from inorganic bases, such as hydroxides, for example LiOH, NaOH or KOH. Bases to which preference is given are hydroxides, such as NaOH or KOH; especially preferred is NaOH.

A suitable amount of base for anion formation is, for example, at least one equivalent relative to compounds of formula II used in step d), preferably from 1 to 5 equivalents; more preferably from 1 to 3 equivalents.

The formation of the anion is preferably carried out in a temperature range of from 10° C. to 100° C., especially from 40° C. to 70° C. The reaction time for anion formation is generally from 15 minutes to 48 hours, preferably from 15 minutes to 18 hours, more preferably 15 minutes to 5 hours or 1 to 5 hours. Said anion formation can be carried out at normal, elevated or reduced pressure, preferably at normal pressure. After formation of the anion, said anion is typically present in the aqueous phase of the reaction mixture.

In one embodiment of the invention, the acid is added leading to an adjustment of the pH of the aqueous phase to a value of 7 or below, preferably 6 or below, more preferably 5 or below.

Suitable acids are inorganic acids, such as hydrochloric acid or sulfuric acid; or organic acids, such as formic acid, acetic acid or propionic acid. Preference is given to inorganic acids and special preference is given to hydrochloric acid.

The acid is added preferably in a temperature range of from 50° C. to 95° C., especially from 80° C. to 95° C.

Process Step f2):

Process step f2) corresponds to process step f1) and differs only in the order of addition. After formation of the anion, said anion is typically present in the aqueous phase of the reaction mixture. In a preferred embodiment of the invention, the aqueous phase is isolated from the organic phase before it is added to the acid.

Process Step f3):

In process step f3) the compound of formula I ("the free acid") is formed directly by acidic saponification.

The acid used in step f3) is typically an inorganic acid, such as hydrochloric acid or sulfuric acid; or an organic acid, such as formic acid, acetic acid or propionic acid. Preference is given to inorganic acids and special preference is given to hydrochloric acid.

A preferable amount of acid is at least 0.01 equivalents relative to compounds of formula II used in step d), more preferably from 0.01 to 5 equivalents; even more preferably from 1 to 5 equivalents, most preferably from 1 to 3 equivalents.

The formation of the free acid is preferably carried out in a temperature range of from 40° C. to 100° C., especially from 40° C. to 60° C. The reaction time is generally from 15 minutes to 48 hours, preferably from 15 minutes to 18 hours, more preferably 15 minutes to 5 hours or 1 to 5 hours. Said free acid formation can be carried out at normal, elevated or reduced pressure, preferably at normal pressure.

As the compound of formula III typically is present in the organic phase after step d), in a preferred embodiment of the invention, the organic phase is isolated from the aqueous phase before the acid is added in step f3).

Isolation of Compound of Formula I after Performing Process Step f1), f2) or f3):

Under typical process conditions described above, the compounds of formula I precipitate and can be easily isolated after performing process steps f1), f2) or f3). Typically this is done by cooling followed by filtration.

Process Step g)

Step g) may be performed according to known methods, e.g. as described in WO 2004/035589 or WO 2009/135860. For example, reacting a compound of formula I with a compound of formula XI may involve treating the compound of formula I with a halogenating agent, such as thionyl chloride, oxalyl chloride, phosgene, $SF_4$, DAST, deoxofluor or thionyl-bromide to provide the acid-halogen, e.g. the acid chloride, which may then be reacted with the compound of formula XI in the presence of a suitable base, e.g. LiOH, KOH, NaOH, $NEt_3$, $NaHCO_3$, $KHCO_3$, $Na_2CO_3$ or $K_2CO_3$, e.g. in a solvent such as toluene, xylenes, dichloromethane, ethyl acetate or DMF, e.g. at −10° C. to 30° C.

EXAMPLES

Example 1

Preparation of 2-[1-Ethoxy-meth-(Z)-ylidene]-4,4-difluoro-3-oxo-butyric acid ethyl ester (Compound of Formula II)

Process step a): 925.1 g (10.5 mol) of ethyl acetate and 263.2 (2.1 mol) of ethyl difluoroacetate (99%) were charged and heated to 40° C. 178.8 g (2.52 mol) of sodium ethoxide (>96%) were metered in at 35-45° C. with stirring in the course of 1 hour. Afterwards, the reaction mixture was stirred at 40° C. for two hours and then cooled to 20° C.

Process step b): To 651.4 g of the aforementioned reaction mixture 58.3 g (1.6 mol) of HCl gas were introduced at 10° C. to 20° C. within one hour. No water was added and the inorganic salts were not removed.

Process step c): 185.3 g (1.25 mol) of triethyl orthoformate were initially charged in a stirred vessel, the pressure in the vessel was reduced to 500 mbar and the triethyl orthoformate was heated to 100° C. 177.5 g (0.25 mol-100% conversion in process steps a) and b) assumed) of ethyl 4,4-difluoroacetoacetate (in the form of a suspension coming from process step b)) were added at 98° C. to 105° C. within 2 hours. Thereafter, the reaction mixture was stirred at 100° C. for further 3.5 hours. Within this post reaction time the pressure was further reduced to 300 mbar. During the whole reaction time low boiling compounds were removed by distillation under reduced pressure. The resulting suspension (191 g) comprised 16.7% (w/w) of the desired product (GC analysis, quantification with internal standard). The yield, based on ethyl difluoroacetate used, was 57.3%.

Example 2

Preparation of 3-difluoromethyl-1-methyl-1H-pyrazole-4-carboxylic acid ethyl ester (Compound of Formula III)

Process steps d) and e): 69.1 g (0.525 mol) of methylhydrazine (in the form of a 35% (w/w) aqueous solution), 16.9 g (0.278 mol) of NaCl and 100 g of xylenes were initially charged and the mixture was tempered at 20° C. Simultaneously, a solution of 119.6 g (92.9%; 0.5 mol) of 2-[1-Ethoxy-meth-(Z)-ylidene]-4,4-difluoro-3-oxo-butyric acid ethyl ester in 200 g of xylenes was prepared. The latter solution was added to the mixture of methylhydrazine, NaCl and xylenes at ca. 20° C. within 30 minutes. Afterwards the reaction mixture was stirred for 15 minutes at 20° C. The lower aqueous phase was separated. The residual organic phase (420.9 g) comprised 19.0% by weight of the desired product (quantitative HPLC analysis).

Example 3

Preparation of 2-[1-Ethoxy-meth-(Z)-ylidene]-4,4-difluoro-3-oxo-butyric acid ethyl ester (Compound of Formula II)

Process step a): 2775.2 g (31.5 mol) of ethyl acetate and 789.7 (6.3 mol) of ethyl difluoroacetate (99%) were charged at 5-10° C. 496.8 g (6.93 mol) of sodium ethoxide (>96%) were metered in at 0-10° C. with stirring in the course of 100 minutes. Afterwards, the reaction mixture was heated to 40° C. and stirred at that temperature for two hours. Then, the reaction mixture was cooled to 0-10° C.

Process step b): 298.5 g (8.19 mol) of HCl gas were introduced at 0° C. to 15° C. within 110 minutes. No water was added and the inorganic salts were not removed. The resulting suspension (4285 g) comprised 23.6% (w/w) of the desired product of value (GC analysis, quantification with internal standard). The yield, based on ethyl difluoroacetate used, was 96.8%.

Process step c): 778.1 g (5.25 mol) of triethyl orthoformate were charged in a stirred vessel, the pressure within the vessel was slowly reduced to 310 mbar and the triethyl orthoformate was heated to 104° C. 121.1 g (0.175 mol-100% conversion in process steps a) and b) assumed) of ethyl 4,4-difluoroacetoacetate (in the form of a suspension coming from process step b)) were added at 103° C. to 104° C. within 2 hours. Thereafter, the reaction mixture was stirred at 105° C. for further 30 minutes. During the entire reaction time low boiling compounds were removed by distillation under reduced pressure. Afterwards, the suspension was cooled down to room temperature. The resulting suspension (761 g) comprised 4.36% (w/w) of the desired product (GC analysis, quantification with internal standard). This corresponds to an overall yield over the two synthetic steps of 85.4%, based on ethyl difluoroacetate used.

Example 4

Preparation of 2-[1-Ethoxy-meth-(Z)-ylidene]-4,4-difluoro-3-oxo-butyric acid ethyl ester (Compound of Formula II)

Process step a): 1189.4 g (13.5 mol) of ethyl acetate and 1128.2 (9 mol) of ethyl difluoroacetate (99%) were charged at 5-10° C. 709.7 g (9.9 mol) of sodium ethoxide (>96%) were metered in at 5-10° C. with stirring in the course of 80 minutes. Afterwards, the reaction mixture was heated to 55° C. and stirred at that temperature for three hours. Then, the reaction mixture was cooled to room temperature and kept overnight.

Process step b): The other day the reaction mixture was heated to 40° C. and 426.5 g (11.7 mol) of HCl gas were introduced at 40° C. within 7 hours. No water was added and the inorganic salts were not removed. The resulting suspension (3400 g) comprised 41.0% (w/w) of the desired product of value (GC analysis, quantification with internal standard). The yield, based on ethyl difluoroacetate used, was 93.3%.

Process step c): 778.1 g (5.25 mol) of triethyl orthoformate were charged in a stirred vessel, the pressure within the vessel was slowly reduced to 170 mbar and the triethyl orthoformate was heated to 92° C. 134.3 g (0.35 mol-100% conversion in process steps a) and b) assumed) of ethyl 4,4-difluoroacetoacetate (in the form of a suspension coming from process step b)) were added at 92° C. to 95° C. within 4 hours. Thereafter, the reaction mixture was stirred at 95° C. for further 30 minutes. During the entire reaction time low boiling compounds were continuously removed by distillation under reduced pressure. Afterwards, the triethyl orthoformate was distilled by lowering the pressure accordingly. The resulting concentrated product suspension was cooled down to room temperature and 70.2 g of xylenes were added. The resulting suspension (178 g) comprised 40.0% (w/w) of the desired product (GC analysis, quantification with internal standard). This corresponds to an overall yield over the two synthetic steps of 91.6%, based on ethyl difluoroacetate used.

The invention claimed is:

1. A process for preparing a compound of formula III

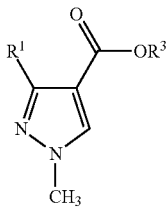

(III)

wherein $R^1$ is $CF_3$, $CF_2H$ or $CFH_2$, and $R^3$ is $C_1$-$C_6$ alkyl, comprising a) reacting compounds of formula (IV), (V) and (VI)

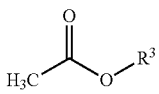

(IV)

wherein $R^3$ is as defined for the compound of formula III, $R^4OM$ (V)

wherein M is a lithium, sodium or potassium ion and $R^4$ is $C_1$-$C_6$ alkyl, and

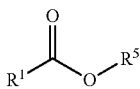

(VI)

wherein $R^1$ is as defined for the compound of formula III and $R^5$ is $C_1$-$C_6$ alkyl,
to form an enolate of formula VII

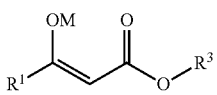

(VII)

wherein M is as defined for formula V and $R^1$ and $R^3$ are as defined for the compound of formula III, and b) releasing the compound of formula VIII

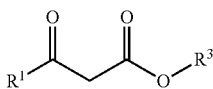

(VIII)

wherein $R^1$ and $R^3$ are as defined for the compound of formula III,
from the enolate of formula VII by means of an acid, c) converting the compound of formula VIII, in the presence of the salt formed from cation M and the anion of the acid in step b), to a compound of formula II,

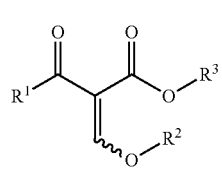

(II)

wherein $R^1$ and $R^3$ are as defined for the compound of formula III and $R^2$ is $C_1$-$C_6$ alkyl, and d) reacting the compound of formula II with methylhydrazine in the presence of water
to form a compound of formula III e) separating the compound of formula III from the salt formed from cation M and the anion of the acid in step b)
wherein step d) is carried out in the presence of a water-immiscible solvent and in step e) the compound of formula III is separated from the salt by separating the organic phase containing the compound of formula III from the aqueous phase containing the salt.

2. A process for preparing a compound of formula III

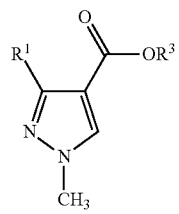

(III)

wherein $R^1$ is $CF_3$, $CF_2H$ or $CFH_2$, and $R^3$ is $C_1$-$C_6$ alkyl, comprising providing a mixture comprising a compound of formula II

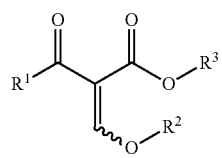

(II)

wherein $R^1$ and $R^3$ are as defined for the compound of formula III and $R^2$ is $C_1$-$C_6$ alkyl, and a salt and performing the steps dd) reacting the mixture comprising the compound of formula II and the salt with methylhydrazine in the presence of water to form a compound of formula III; and ee) separating the compound of formula III from the salt;
wherein step dd) is carried out in the presence of a water-immiscible solvent and in step ee) the compound of formula III is separated from the salt by separating the organic phase containing the compound of formula III from the aqueous phase containing the salt; and wherein the salt is one in which the cation is a lithium, sodium or potassium salt of chloride, bromide, iodide, sulphate, phosphate, nitrate, formate, acetate, propionate, citrate, oxalate, methanesulfonate or p-toluenesulfonate.

3. A process according to claim 1, comprising the step f) converting the compound of formula III to a compound of formula I

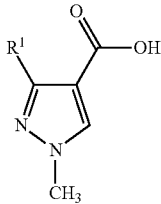

(I)

wherein $R^1$ is as defined for the compound of formula III.

4. A process for preparing a compound of formula III

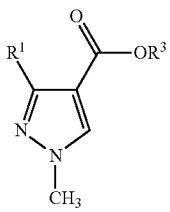

(III)

wherein $R^1$ is $CF_3$, $CF_2H$ or $CFH_2$, and $R^3$ is $C_1$-$C_6$ alkyl, comprising providing a mixture comprising a compound of formula II

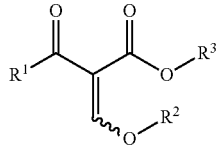

(II)

wherein $R^1$ and $R^3$ are as defined for the compound of formula III and $R^2$ is $C_1$-$C_6$ alkyl, and a salt and performing the steps dd) reacting the mixture comprising the compound of formula II and the salt with methylhydrazine in the presence of water to form a compound of formula III; and ee) separating the compound of formula III from the salt; wherein step dd) is carried out in the presence of a water-immiscible solvent and in step ee) the compound of formula III is separated from the salt by separating the organic phase containing the compound of formula III from the aqueous phase containing the salt;

wherein the mixture comprising the compound of formula II and the salt is a suspension in which the salt is a solid.

5. A process according to claim 1, wherein in step b) the release of the compound of formula VIII from the enolate of formula VII is carried out substantially in the absence of water.

6. A process according to claim 1, wherein in step c) the compound of formula VIII is converted to a compound of formula II in the absence of an acid anhydride.

7. A process according to claim 1, wherein the compound of formula VIII is converted to a compound of formula II using a molar excess of orthoester of at least 10:1 compared to the compound of formula VIII.

\* \* \* \* \*